United States Patent
Shah et al.

(10) Patent No.: US 9,737,694 B1
(45) Date of Patent: Aug. 22, 2017

(54) MULTI-LAYER FILM WELDED ARTICULATED BALLOON

(71) Applicant: Polyzen Inc., Apex, NC (US)

(72) Inventors: Tilak M. Shah, Cary, NC (US); Christopher D. Strom, Cary, NC (US)

(73) Assignee: POLYZEN INC., Apex, NC (US)

( * ) Notice: Subject to any disclaimer, the term of this patent is extended or adjusted under 35 U.S.C. 154(b) by 0 days.

(21) Appl. No.: 15/336,122

(22) Filed: Oct. 27, 2016

Related U.S. Application Data (63) Continuation of application No. 14/657,857, filed on Mar. 13, 2015, now abandoned, which is a
(Continued)

(51) Int. Cl.
*A61M 25/16* (2006.01)
*A61M 25/10* (2013.01)
(Continued)

(52) U.S. Cl.
CPC .... *A61M 25/1029* (2013.01); *A61M 25/1002* (2013.01); *A61M 39/24* (2013.01); *B29C 65/04* (2013.01); *B29C 66/1122* (2013.01); *B29C 66/21* (2013.01); *B29C 66/4312* (2013.01); *B29C 66/4742* (2013.01);
(Continued)

(58) Field of Classification Search
CPC .......... A61M 25/1029; A61M 25/1002; B29C 65/04
See application file for complete search history.

(56) References Cited

U.S. PATENT DOCUMENTS

| | | | |
|---|---|---|---|
| 2,703,770 | A | 3/1955 | Melzer |
| 3,164,151 | A | 1/1965 | Nicoll |
| | | (Continued) | |

FOREIGN PATENT DOCUMENTS

| | | |
|---|---|---|
| JP | 51-90376 | 8/1976 |
| JP | 51-90376 A | 8/1976 |
| | (Continued) | |

OTHER PUBLICATIONS

"Polyzen Corrected Opposition to Radiadyne Combined Motion to Dismiss and to Correct Inventorship Filed on Jan. 24, 2012 in U.S. Dist. Court East. Dist. of NC West. Div. Case No. 5:11-cv-00662-D, including Exhibits A—L and Affidavits", , pp. 1-24, No. 17.
(Continued)

*Primary Examiner* — Jeff Aftergut
(74) *Attorney, Agent, or Firm* — Hultquist, PLLC; Steven J. Hultquist (57) ABSTRACT

A method of fabrication of a medical balloon, and a balloon device useful for various medical balloon procedures, such as gastrointestinal, vascular, reproductive system, urinary system and pulmonary applications. At least two layers of a thermoplastic film are sealed at their peripheral edges and heat sealed at one or more locations inside an area enclosed by the sealed edges at predetermined locations, in one implementation of the balloon device. Such configuration enables the balloon to articulate to a desired shape upon inflation, with the desired shape being selected to accommodate a specific medical application.

30 Claims, 5 Drawing Sheets

Related U.S. Application Data continuation of application No. 14/645,223, filed on Mar. 11, 2015, which is a continuation of application No. 13/685,448, filed on Nov. 26, 2012, which is a continuation of application No. 13/154,229, filed on Jun. 6, 2011, now Pat. No. 8,740,845, which is a continuation of application No. 12/237,897, filed on Sep. 25, 2008, now Pat. No. 7,976,497.

(60) Provisional application No. 60/974,884, filed on Sep. 25, 2007.

(51) Int. Cl.
 A61M 39/24 (2006.01)
 B29C 65/04 (2006.01)
 B29C 65/00 (2006.01)
 B29K 101/12 (2006.01)
 B29L 9/00 (2006.01)
 B29L 22/02 (2006.01)
 B29L 31/00 (2006.01)

(52) U.S. Cl.
 CPC ......... *B29C 66/73521* (2013.01); *A61M 2025/1075* (2013.01); *A61M 2210/166* (2013.01); *B29K 2101/12* (2013.01); *B29K 2995/0046* (2013.01); *B29L 2009/00* (2013.01); *B29L 2022/022* (2013.01); *B29L 2031/753* (2013.01)

(56) References Cited

U.S. PATENT DOCUMENTS

| | | |
|---|---|---|
| 3,674,019 A | 7/1972 | Grant |
| 4,043,345 A | 8/1977 | Kramann et al. |
| 4,311,146 A | 1/1982 | Wonder |
| 4,327,736 A | 5/1982 | Inoue |
| 4,347,633 A | 9/1982 | Gammons et al. |
| 4,483,030 A | 11/1984 | Flick et al. |
| 4,523,584 A | 6/1985 | Yachia et al. |
| 4,555,242 A | 11/1985 | Saudagar |
| 4,650,463 A | 3/1987 | LeVeen et al. |
| 4,784,133 A | 11/1988 | Mackin |
| 4,994,033 A | 2/1991 | Shockey et al. |
| 5,014,695 A | 5/1991 | Benak et al. |
| 5,022,109 A | 6/1991 | Pekar |
| 5,116,310 A | 5/1992 | Seder et al. |
| 5,133,776 A | 7/1992 | Crowder |
| 5,209,799 A | 5/1993 | Vigil |
| 5,219,792 A | 6/1993 | Kim et al. |
| 5,234,454 A | 8/1993 | Bangs |
| 5,304,135 A | 4/1994 | Shonk |
| 5,309,896 A | 5/1994 | Moll et al. |
| 5,355,087 A | 10/1994 | Claiborne et al. |
| 5,360,414 A | 11/1994 | Yarger |
| 5,369,828 A | 12/1994 | Graebe |
| 5,388,292 A | 2/1995 | Stinson et al. |
| 5,433,252 A | 7/1995 | Wolf et al. |
| 5,449,371 A | 9/1995 | Pinchuk et al. |
| 5,451,232 A | 9/1995 | Rhinehart et al. |
| 5,458,572 A | 10/1995 | Campbell et al. |
| 5,512,051 A | 4/1996 | Wang et al. |
| 5,527,280 A | 6/1996 | Goelz |
| 5,545,122 A | 8/1996 | Spruill |
| 5,545,220 A | 8/1996 | Andrews et al. |
| 5,598,593 A | 2/1997 | Wolfe |
| 5,679,423 A | 10/1997 | Shah |
| 5,704,913 A | 1/1998 | Abele et al. |
| 5,716,329 A | 2/1998 | Dieter |
| 5,743,852 A | 4/1998 | Johnson |
| 5,776,159 A | 7/1998 | Young |
| 5,782,800 A | 7/1998 | Yoon |
| 5,833,915 A | 11/1998 | Shah |
| 5,843,116 A | 12/1998 | Crocker et al. |
| 5,855,588 A | 1/1999 | Young |
| 5,865,729 A | 2/1999 | Meehan et al. |
| 5,868,705 A | 2/1999 | Bagaoisan et al. |
| 5,868,776 A | 2/1999 | Wright |
| 5,879,499 A | 3/1999 | Corvi |
| 5,890,245 A | 4/1999 | Klearman et al. |
| 5,924,456 A | 7/1999 | Simon |
| 5,935,115 A | 8/1999 | Espina |
| 5,947,991 A | 9/1999 | Cowan |
| 5,951,514 A | 9/1999 | Sahota |
| 5,996,639 A | 12/1999 | Gans et al. |
| 6,015,382 A | 1/2000 | Zwart et al. |
| 6,022,313 A | 2/2000 | Ginn et al. |
| 6,066,154 A | 5/2000 | Reiley et al. |
| 6,102,929 A | 8/2000 | Conway et al. |
| 6,110,142 A | 8/2000 | Pinchuk et al. |
| 6,120,523 A | 9/2000 | Crocker et al. |
| 6,156,053 A | 12/2000 | Ghandi et al. |
| 6,217,548 B1 | 4/2001 | Tsugita et al. |
| 6,249,708 B1 | 6/2001 | Nelson et al. |
| 6,291,543 B1 | 9/2001 | Shah |
| 6,312,462 B1 | 11/2001 | McDermott et al. |
| 6,352,077 B1 | 3/2002 | Shah |
| 6,371,910 B1 | 4/2002 | Zwart et al. |
| 6,409,741 B1 | 6/2002 | Crocker |
| 6,460,541 B1 | 10/2002 | Shah et al. |
| 6,478,029 B1 | 11/2002 | Boyd et al. |
| 6,478,789 B1 | 11/2002 | Spehalski et al. |
| 6,510,574 B2 | 1/2003 | Sharrock et al. |
| 6,520,977 B2 | 2/2003 | Piraka |
| 6,663,646 B1 | 12/2003 | Shah |
| 6,712,832 B2 | 3/2004 | Shah |
| 6,733,512 B2 | 5/2004 | McGhan |
| 6,746,465 B2 | 6/2004 | Diederich et al. |
| 6,805,662 B2 | 10/2004 | Shah et al. |
| 6,827,710 B1 | 12/2004 | Mooney et al. |
| 6,875,193 B1 | 4/2005 | Bonnette et al. |
| 6,939,339 B1 | 9/2005 | Axexandersen et al. |
| 6,942,679 B1 | 9/2005 | Terai |
| 6,981,980 B2 | 1/2006 | Sampson et al. |
| 7,041,056 B2 | 5/2006 | Deslauriers et al. |
| 7,112,186 B2 | 9/2006 | Shah |
| 7,121,915 B2 | 10/2006 | Banks |
| 7,470,251 B2 | 12/2008 | Shah |
| 7,666,205 B2 | 2/2010 | Weikel et al. |
| 7,976,497 B2 | 7/2011 | Shah et al. |
| 2001/0011174 A1 | 8/2001 | Reiley et al. |
| 2003/0028097 A1 | 2/2003 | D'Amico et al. |
| 2003/0028211 A1 | 2/2003 | Crocker et al. |
| 2003/0029182 A1 | 2/2003 | Augustine et al. |
| 2003/0088209 A1 | 5/2003 | Chiu et al. |
| 2003/0105481 A1 | 6/2003 | Fogarty et al. |
| 2004/0064089 A1 | 4/2004 | Kesten et al. |
| 2005/0015047 A1 | 1/2005 | Shah |
| 2005/0222329 A1 | 10/2005 | Shah |
| 2006/0212064 A1 | 9/2006 | Shah |
| 2007/0010845 A1 | 1/2007 | Gong et al. |
| 2007/0212559 A1 | 9/2007 | Shah |
| 2007/0239110 A1 | 10/2007 | Shah |
| 2007/0299463 A1 | 12/2007 | Shah |
| 2008/0086083 A1 | 4/2008 | Towler |
| 2008/0172080 A1 | 7/2008 | Isham |
| 2008/0188802 A1 | 8/2008 | Shah |
| 2008/0262449 A1 | 10/2008 | Shah et al. |
| 2008/0262450 A1 | 10/2008 | Shah et al. |
| 2009/0082724 A1* | 3/2009 | Shah ............... A61M 25/1002 604/103.08 |
| 2010/0137797 A2 | 6/2010 | Shah, T. et al. |
| 2011/0295202 A1 | 12/2011 | Shah et al. |
| 2013/0085324 A1 | 4/2013 | Shah et al. |
| 2013/0123621 A1* | 5/2013 | Isham ............... A61N 5/1049 600/435 |
| 2015/0182229 A1 | 7/2015 | Shah et al. |
| 2015/0190142 A1 | 7/2015 | Shah et al. |

FOREIGN PATENT DOCUMENTS

| | | |
|---|---|---|
| JP | 51-100833 A | 9/1976 |
| JP | 51-101084 | 9/1976 |

(56) References Cited

FOREIGN PATENT DOCUMENTS

| JP | 51-101084 A | 9/1976 |
|---|---|---|
| JP | 63-84565 A | 4/1988 |
| JP | 04-129570 | 4/1992 |
| JP | 04-129570 A | 4/1992 |
| JP | 10-127771 A | 5/1998 |
| WO | 9814123 A1 | 4/1998 |
| WO | 9920321 A2 | 4/1999 |

OTHER PUBLICATIONS

"Radiadyne Reply in Support of Its Combined Motion to Dismiss Under Rule 12(B)(1) and to Correct Inventorship Filed on Jan. 27, 2012 in U.S. Dist. Court East. Dist. of NC West. Div. Case No. 5:11-cv-00662-D, without exhibits", , pp. 1-11, No. 19.

"Polyzen and Radiadyne Joint Claim Construction Statement Filed on Apr. 12, 2013 in U.S. Dist. Court East. Dist. of NC West. Div. Case No. 5:11-cv-00662-D, including Claim Construction Chart Exhibit", pp. 117, No. 41.

"Plaintiff Polyzen Opening Brief on Claim Construction Filed on Apr. 30, 2013 in U.S. Dist. Court East. Dist. of NC West. Div. Case No. 5:11-cv-00662-D, including Exhibits A—U", , pp. 1-254, No. 55.

"Radiadyne Opening Claim Construction Brief Filed on Apr. 30, 2013 in U.S. Dist. Court East. Dist. of NC West. Div. Case No. 5:11-cv-00662-D, including Declaration T. Morrow with Exhibits A—G", , pp. 1-103, No. 54.

"Polyzen Responsive Claim Construction Brief Filed on May 21, 2013 in U.S. Dist. Court East. Dist. of NC West. Div. Case No. 5:11-cv-00662-D", , pp. 1-11, No. 63.

"Radiadyne Responsive Claim Construction Brief Filed on May 21, 2013 in U.S. Dist. Court East. Dist. of NC West. Div. Case No. 5:11-cv-00662-D, including Exhibit", , pp. 1-36, No. 62.

"Polyzen Reply Claim Construction Brief Filed on May 31, 2013 in U.S. Dist. Court East. Dist. of NC West. Div. Case No. 5:11-cv-00662-D, including Exhibit", , pp. 1-21, No. 64.

"Polyzen Cross Motion for Summary Judgment on Radiadyne Affirmative Defense of Co-Inventorship Filed on Jun. 28, 2013 in U.S. Dist Court East. Dist. of NC West. Div. Case No. 5:11-cv-00662-D", , pp. 1-3, No. 72.

"Polyzen Memo. of Law in Opposition to Radiadyne Motion for Summary Judgment of Co-Inventorship and in Support Cross Motion Filed on Jun. 28, 2013 in U.S. Dist. Court East. Dist. of NC West. Div. Case No. 5:11-cv-00662-D, including Exhibits A—M", pp. 1-93, No. 73.

"Answer of Defendant and Counter-Plaintiff Radiadyne Filed on Oct. 1, 2012 in U.S. Dist. Court East. Dist. of NC West. Div. Case No. 5:11-cv-00662-D", , pp. 1-8, No. 32.

"Oct. 8, 2013 Office Action issued in U.S. Appl. No. 13/685,448 by Pritesh Ashok Patel".

"Office Action Issued on Oct. 11, 2012 in U.S. Appl. No. 13/154,229 by Pritesh A. Patel".

"Oct. 28, 2013 Office Action issued in U.S. Appl. No. 13/685,448 by Pritesh Ashok".

"Order Issued on Oct. 31, 2013 in U.S. Dist. Court East. Dist. of NC West. Div. Case No. 5:11-cv-00662-D", , pp. 1-2, No. 88.

"Polyzen First Amended Complaint Filed on Nov. 4, 2013 in U.S. Dist. Court East. Dist. of NC West. Div. Case No. 5:11-cv-00662-D", , pp. 1-16, No. 89.

"Answer of Defendant and Counter-Plaintiff Radiadyne to Polyzen First Amended Complaint Filed on Nov. 18, 2013 in U.S. Dist. Court East. Dist. of NC West. Div. Case No. 5:11-cv-00662-D", , pp. 1-29, No. 91.

"Polyzen Complaint Against Radiadyne Filed on Nov. 21, 2011 in U.S. Dist. Court East. Dist. of NC West. Div. Case No. 5:11-cv-00662-D, including Exhibits A, B, and C", , pp. 1-22, No. 1.

"Civil Action No. 5:11-CV-0062-D, U.S. District Court for the Eastern District of North Carolina, Western Division; filed Nov. 21, 2011; pending litigation."

"Radiadyne Motion to Dismiss and Correct Inventorship Filed on Dec. 13, 2011 in U.S. Dist. Court East. Dist. of NC West. Div. Case No. 5:11-cv-00662-D, including Exhibits A, B, C, D, and F", , pp. 1-48, No. 10.

"Polyzen Complaint Against Radiadyne Filed on Jun. 3, 2014 in U.S. Dist. Court East. Dist. of NC West. Div. Case No. 5:14-cv-00323-F, including Exhibits A, B, and C", , pp. 1-25, No. 1.

"May 22, 2015 Office Action issued in U.S. Appl. No. 13/685,448 by Anh T. Bui".

* cited by examiner

MULTI-LAYER FILM WELDED ARTICULATED BALLOON

CROSS-REFERENCE TO RELATED APPLICATIONS

This application is a continuation under 35 U.S.C. §120 of U.S. patent application Ser. No. 14/657,857 filed Mar. 13, 2015 in the names of TILAK M. SHAH and CHRISTOPHER D. STROM for "Multi-Layer Film Welded Articulated Balloon," which is a continuation under 35 U.S.C. §120 of U.S. patent application Ser. No. 14/645,223 filed Mar. 11, 2015 in the names of TILAK M. SHAH and CHRISTOPHER D. STROM for "Multi-Layer Film Welded Articulated Balloon," which is a continuation under 35 U.S.C. §120 of U.S. patent application Ser. No. 13/685,448 filed Nov. 26, 2012 in the names of TILAK M. SHAH and CHRISTOPHER D. STROM for "Multi-Layer Film Welded Articulated Balloon," which is a continuation under 35 U.S.C. §120 of U.S. patent application Ser. No. 13/154,229 filed Jun. 6, 2011 in the names of TILAK M. SHAH and CHRISTOPHER D. STROM for "Multi-Layer Film Welded Articulated Balloon" and issued Jun. 3, 2014 as U.S. Pat. No. 8,740,845, which is a continuation under 35 U.S.C. §120 of U.S. patent application Ser. No. 12/237,897 filed Sep. 25, 2008 in the names of TILAK M. SHAH and CHRISTOPHER D. STROM for "Multi-Layer Film Welded Articulated Balloon" and issued Jul. 12, 2011 as U.S. Pat. No. 7,976,497, which in turn claims the benefit under 35 U.S.C. §119 of U.S. Provisional Patent Application No. 60/974,884 filed Sep. 25, 2007 in the names of TILAK M. SHAH and CHRISTOPHER D. STROM for "Multi-Layer Film Welded Articulated Balloon." The disclosures of each of the foregoing U.S. patent application Ser. Nos. 14/657,857, 14/645,223 and 13/685,448, U.S. Pat. Nos. 8,740,845 and 7,976,497, and U.S. Provisional Patent Application No. 60/974,884 are hereby incorporated herein by reference, in their respective entireties, for all purposes.

BACKGROUND OF THE INVENTION

Field of the Invention

The present invention relates to low pressure medical balloon articles and to the methodology for making the same, and in particular to a medical balloon useful for in vivo luminal medical procedures.

Description of the Prior Art

Various balloon articles are in use for cardiovascular and other medical procedures (such as percutaneous transluminal angioplasty, percutaneous transluminal nephrostomy, urethral dilatation, biliary duct dilatation, percutaneous transluminal renal angioplasty, and the like). Balloons may be utilized for such procedures, that are inflatable or otherwise capable of holding pressure. Pressure levels of balloons may be widely varied, depending on the specific application, and may for example be in a range of from 30-150 pounds per square inch (psi) for higher pressures and balloons and 1-10 psi for low pressure balloons.

Low pressure balloons are there which can hold a pressure on the order of 1-3 psi. Low pressure balloons are typically used for gastrointestinal applications. In other applications, balloons are employed in cardiovascular applications for blocking blood flow, or for removing/blocking a blood clot. In such applications, the balloon is typically bonded to the shaft of a catheter, and after inflation and use, the balloon is readily retracted to an original catheter sleeve shape.

An issue confronting the use of balloon articles for in vivo usage is the asymmetric character of the inflation.

There have been various attempts to shape the balloon so it can be articulated after inflation in vivo for its intended use. For example, in angioplasty applications, clots found in arteries should be held against the artery walls until treated or removed. In prostate treatments it is often desirable to space the prostate from the rectum while treating the same with radiation.

Usually, to achieve the desired inflated shape in low pressure balloons, the balloon material, often latex, is prestretched so as to achieve the desired final shape or the balloon has discrete portions which are overinflated so as to assume a desired shape after insertion and inflation. Another tactic employed is to precure particular selected balloon material so that when inflated, the balloon will assume the precured shape, or to form the balloon with a wall thickness which may vary at different locations in the balloon so as to expand at different rates to achieve different shaped portions in the balloon.

While the resultant balloon would be operational for its intended purpose, each requires an involved fabrication methodology.

SUMMARY OF THE INVENTION

The present invention relates to balloon articles useful in various medical procedures.

In one aspect, the present invention provides a method of fabrication of a medical balloon which uses at least two layers of a thermoplastic film sealed at their edges or periphery and heat sealed at one or more locations inside the area enclosed by the sealed edge at preselected locations, which enables the balloon to articulate to a desired shape upon inflation, with the specific shape being dependent on the particular medical application. The layers may have a different thickness or modulus of elasticity or any combination thereof or the same thickness and modulus, and different dimensioned channels formed by the heat sealed locations to articulate to a desired shape.

In a specific aspect, the invention relates to a method for the fabrication of an articulated medical balloon device comprising the steps of:

(a) providing at least two film layers having opposed edges;

(b) sealing said opposed edges to form a compartment adapted to receive fluid to expand said film layers relative to each other;

(c) providing an opening in said fluid compartment that is adapted to receive a lumen; and (d) forming a subcompartment between the sealed edges of said compartment of a predetermined shape and dimension by sealing at least one of said layers to another, intermediate said opposed edges.

In a further aspect, the invention relates to a medical balloon device, comprising:

at least one film layer having an edge secured to a second film layer to form a fluid compartment therebetween, and portions of said film layers between said edges being secured intermediate said edges to form a plurality of subcompartments, and said fluid compartment being provided with an opening to receive a lumen.

Additional aspects, features and embodiments will be more fully apparent from the ensuing disclosure and appended claims.

DETAILED DESCRIPTION OF THE PREFERRED EMBODIMENTS

Figure 1:
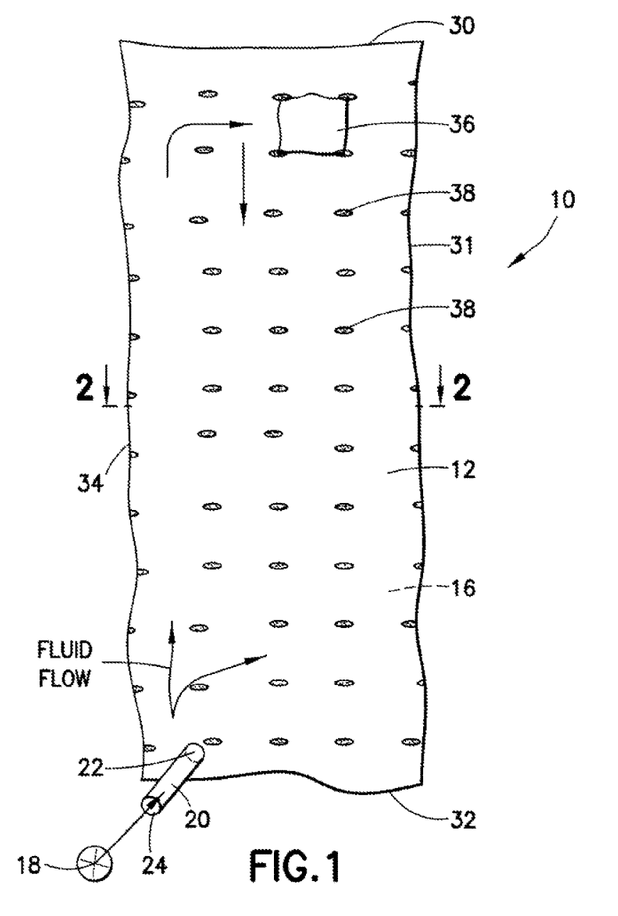
FIG. 1 is a top plan view of one embodiment of the balloon of the present invention.

Referring now to the drawings in detail, wherein like numerals indicate like elements throughout the several views, each of the inflatable balloon structures of the present invention, e.g., the balloon structure 10 of FIG. 1, comprises a multilayer arrangement of film layers 12, 14 or more, that includes an inflatable compartment 16 defining an enclosed interior volume and an anti-reflux valve 18 positioned in a lumen or fluid passage 20 whose distal end 22 is sealingly connected to the interior volume of compartment 16. An inflation bulb is connected to the proximal end 24 of lumen 20 upstream from the anti-reflux valve 18. The valve 18 may be a one-way check valve or a rotatable stem in a housing having an opening adapted to be rotated into alignment with the bore of the lumen 20.

Figure 2:
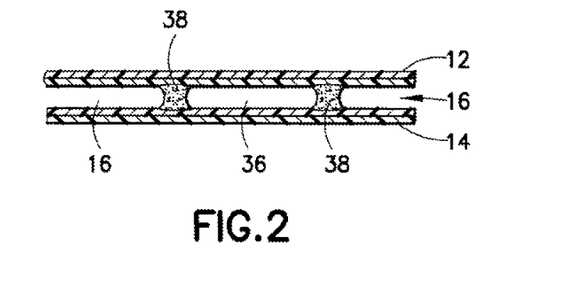
FIG. 2 is a cross-sectional view of the balloon of FIG. 1 taken substantially along the plane indicated by the line 2-2 of FIG. 1.

Oppositely facing film layers 12, 14 are bonded to one another along their edges 30, 31, 32 and 34 to form the inflatable compartment 16 and the compartment 16 is divided into subcompartments 36 by tack or spot welds 38 so that the subcompartments 36 are virtually square-shaped in plan so that upon inflation, the balloon compartment 16 will resemble a tufted cushion with the tack or spot welds 38 forming raised square-shaped subcompartments. This device can be used to separate two organs in the body in vivo and support the same in spaced relation.

The inflatable balloon compartment and subcompartments can be readily formed by heat-sealing or other joining techniques commonly known and used in the art for forming structural articles from thermoplastic film materials in the form of web or sheet stock. For example, RF welding, heat impulse welding, solvent welding, adhesive bonding and the like can be employed.

Figure 3:
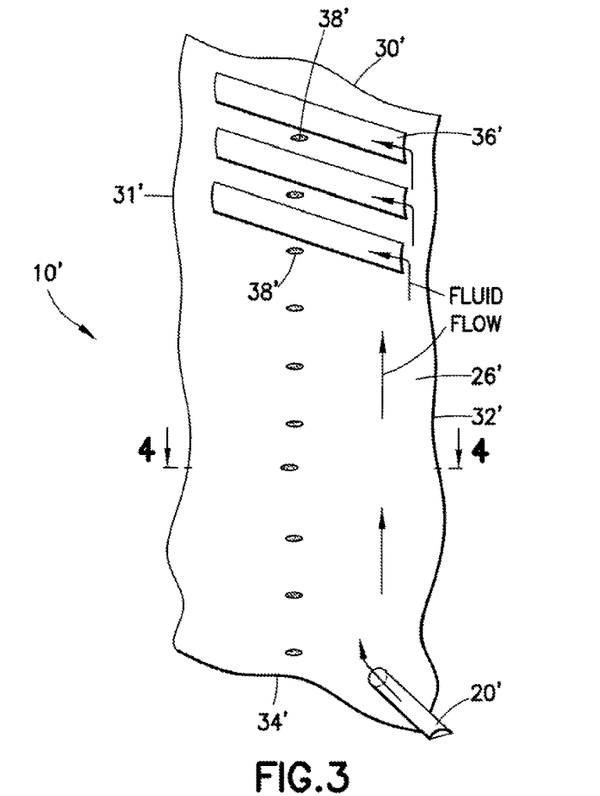
FIG. 3 is a top plan view of a second embodiment of the balloon of the present invention.
Figure 4:
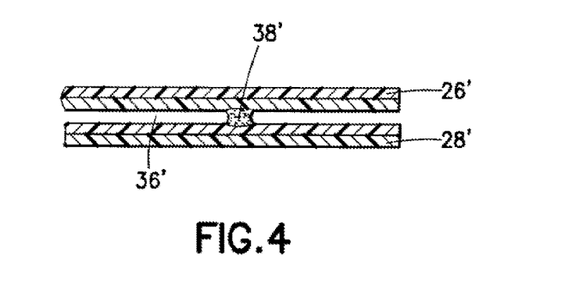
FIG. 4 is a cross-sectional view of the balloon of FIG. 3 taken substantially along the plane indicated by the line 4-4 of FIG. 3.
Figure 5:
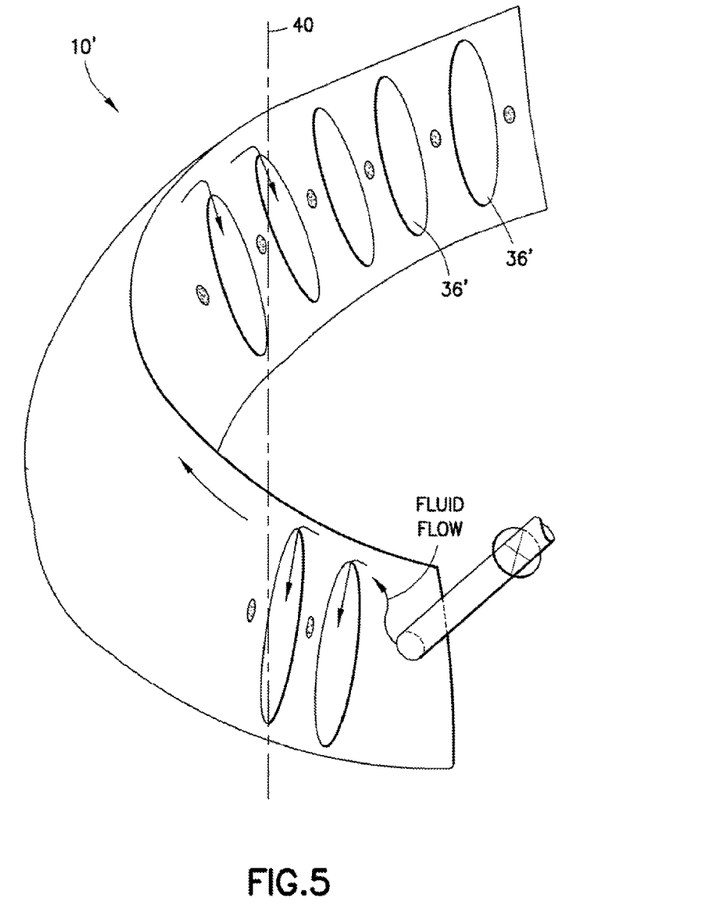
FIG. 5 is a perspective view of the articulated balloon of FIG. 3 after inflation.

Referring to the embodiment of the invention illustrated in FIGS. 3 to 5, inclusive, the film layers 26' and 28' may be bonded to each other in the shape of a parallelogram, with subcompartments 36' extending in spaced relation to each other, but parallel to the side edges 30' and 34' and at an angle to the opposite edges 31' and 32' by tack or spot welds 38'. As shown in FIG. 5, upon inflation, the fluid force introduced into the subcompartments 36' will cause the balloon device 10' to curl into a spiral about a longitudinal axis 40.

Figure 6:
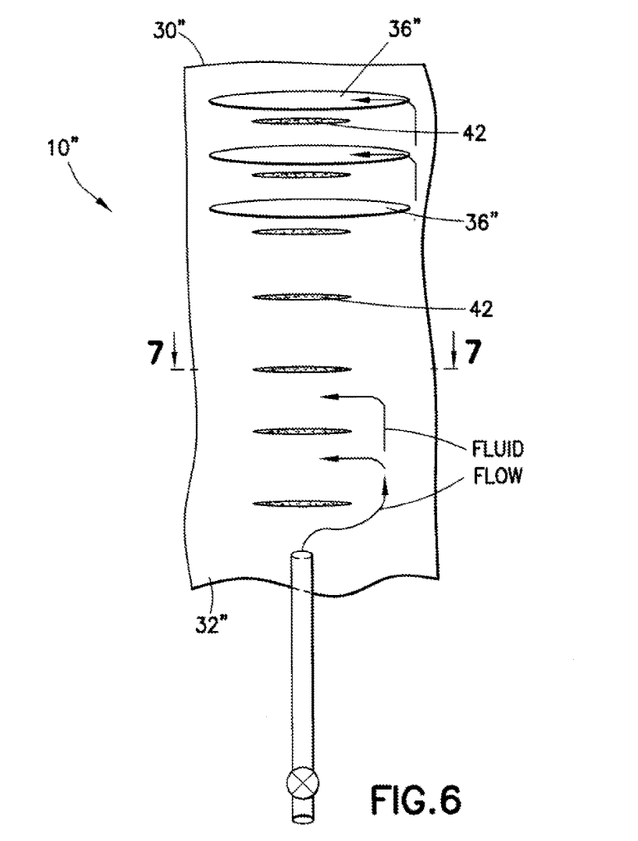
FIG. 6 is a top plan view of yet another embodiment of the balloon of the present invention.
Figure 7:
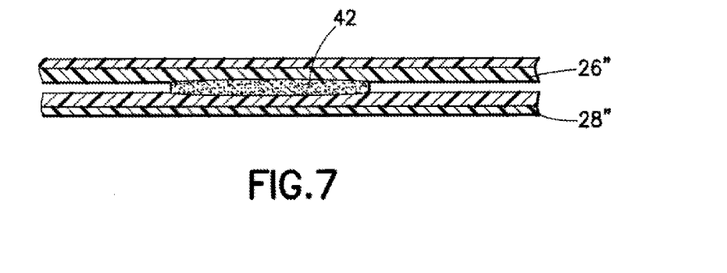
FIG. 7 is a cross-sectional view of the balloon of FIG. 6 taken substantially along the plane indicated by line 7-7 of FIG. 6.

Referring to FIGS. 6 and 7, the balloon device 10" with film layers 26" and 28" can be formed with rectangular subcompartments 36" utilizing line welds 42, parallel to edges 30" and 32".

Figure 8:
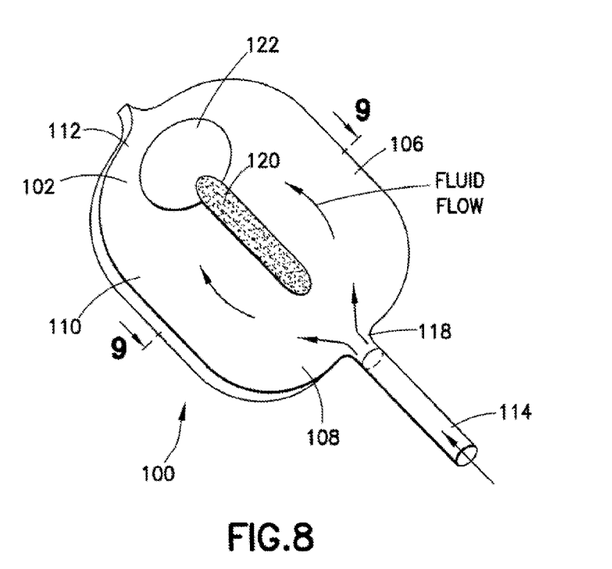
FIG. 8 is a perspective view of still another embodiment of an articulated balloon according to the present invention.
Figure 9:
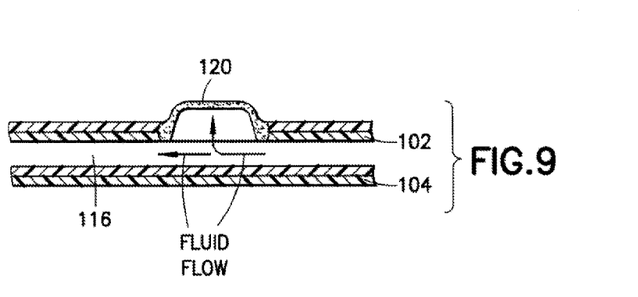
FIG. 9 is a cross-sectional view of the balloon of FIG. 8 taken substantially along the plane indicated by line 9-9 of FIG. 8.

As shown in the embodiment illustrated in FIGS. 8 and 9, the balloon device 100 has thermoplastic film layers 102 and 104 having different properties joined along their edges 106, 108, 110, and 112. For example, the materials can have a different modulus of elasticity, meaning that they will stretch under pressure at different rates to form a particular arcuate or curved shape. In this embodiment, the lumen 114 can extend into the interior of the compartment 116 formed by the film layers 102 and 104 and sealed to the balloon at neck 118.

Additionally, a third layer or strip of film 120 can be added or joined to the top layer 102 to increase its thickness. This will cause the sides 108, 112 to be drawn inwardly relative to the lumen axis, upon inflation, while the distal or forward portion of the compartment 122 will bulge upwardly. Such a device is useful in prostate surgery to support the prostate in spaced relation to other organs.

It will therefore be appreciated that the medical balloon device of the invention may be widely varied in construction and features. In one embodiment, the balloon device includes at least one neck member in a sealing area of the device. The device in a further embodiment comprises at least one area outside of the secured edges forming an inflation port.

While the invention has been illustratively shown and described with respective to particular embodiments, it will be appreciated that the application is not thus limited, but rather extends to and encompasses other variations, modifications and additional embodiments as will be apparent to those of ordinary skill in the art, based on the disclosure herein. Accordingly, the invention is intended to be broadly construed with respect to the ensuing claims, as encompassing all such additional variations, modifications and alternative embodiments.

What is claimed is:

1. A method for the fabrication of an articulable medical balloon device configured for use in an in vivo medical procedure, said method comprising the steps of (a) providing at least two elongate film layers having opposed peripheral edges; (b) sealing said opposed peripheral edges to form an elongate compartment adapted to receive fluid to expand said film layers relative to each other, said elongate compartment having a closed distal end and a proximal neck portion; (c) providing an opening at said proximal neck portion of said elongate fluid compartment that is adapted to receive a lumen so that the lumen is aligned with an elongate direction of the elongate compartment; and (d) sealing at least one of said layers to a third layer, intermediate said opposed peripheral edges, to form a subcompartment in fluid communication with said compartment that is configured to enable the device to articulate to a predetermined shape and dimension for said in vivo medical procedure, said predetermined shape comprising an upwardly bulging distal portion of the elongate compartment, wherein said two elongate film layers are sealed to one another at peripheral edges thereof.

2. The method of claim 1, wherein said sealing steps are performed by welding one layer to another.

3. The method of claim 2, wherein said welding comprises radio frequency (RF) welding.

4. The method of claim 1, wherein two layers of film are provided.

5. The method of claim 1, wherein three layers of film are provided.

6. The method of claim 1, wherein each of said at least two elongate film layers comprises thermoplastic film.

7. The method of claim 1, further comprising sealing said lumen to said neck portion of the medical balloon device.

8. The method of claim 1, wherein said subcompartments are configured to enable the device to articulate to a predetermined shape and dimension to support a prostate in spaced relation to other organs in prostate surgery.

9. The method of claim 1, wherein said lumen has a lumen axis, and wherein the medical balloon device is constructed and arranged so that inflation of the elongate compartment causes sides of the medical balloon device to be drawn inwardly relative to said lumen axis.

10. The method of claim 7, further comprising disposing a valve in said lumen.

11. The method of claim 10, wherein said valve comprises an anti-reflux valve.

12. The method of claim 1, wherein the at least two elongate film layers comprises at least two layers having different properties from one another.

13. The method of claim 12, wherein said different properties comprise different thickness.

14. The method of claim 12, wherein said different properties comprise different modulus of elasticity.

15. The method of claim 12, wherein said different properties comprise different thickness and different modulus of elasticity.

16. The method of claim 1, wherein the medical balloon device is a low-pressure medical balloon device.

17. The method of claim 1, wherein the elongate compartment and subcompartments are constructed and arranged so that the medical balloon device articulates to said predetermined shape at pressure of said fluid in a range of from 1 to 10 pounds per square inch (psi).

18. The method of claim 1, wherein the elongate compartment and subcompartments are constructed and arranged so that the medical balloon device articulates to said predetermined shape at pressure of said fluid in a range of from 1 to 3 pounds per square inch (psi).

19. A method of fabricating an articulable prostate surgery balloon device, said method comprising:
sealing opposed peripheral edges of at least two elongate film layers to form an elongate compartment adapted to receive fluid to expand said film layers relative to each other, said elongate compartment having a closed distal end and a proximal neck portion;
providing an opening at said proximal neck portion of said elongate fluid compartment that is adapted to receive a fluid inflation lumen so that said lumen is aligned with an elongate direction of the elongate compartment;
sealing said lumen to said neck portion of the prostate surgery balloon device so that said lumen is aligned with the elongate direction of the elongate compartment, wherein said lumen has a lumen axis aligned with a longitudinal axis of the elongate compartment; and
sealing at least one of said layers to a third layer, intermediate said opposed peripheral edges, to form a subcompartment in fluid communication with said compartment that is ere configured to enable the prostate surgery balloon device to articulate to a predetermined shape and dimension for prostate surgery upon fluid inflation of the device, said predetermined shape comprising an upwardly bulging distal portion of the elongate compartment.

20. The method of claim 19, wherein said sealing of opposed peripheral edges of at least two elongate film layers comprises at least one selected from the group consisting of radio frequency (RF) welding, heat impulse welding, solvent welding, and adhesive bonding.

21. The method of claim 19, wherein said sealing of opposed peripheral edges of at least two elongate film layers comprises RF welding.

22. The method of claim 19, wherein said sealing of at least one of said layers to another, intermediate said opposed peripheral edges, to form subcompartments comprises at least one selected from the group consisting of radio frequency (RF) welding, heat impulse welding, solvent welding, and adhesive bonding.

23. The method of claim 19, wherein said sealing of at least one of said layers to another, intermediate said opposed peripheral edges, to form subcompartments comprises RF welding.

24. The method of claim 19, wherein said sealing of opposed peripheral edges of at least two elongate film layers, and said sealing of at least one of said layers to another, intermediate said opposed peripheral edges, to form subcompartments, each comprise RF welding.

25. The method of claim 19, performed with two elongate film layers.

26. The method of claim 19, performed with three elongate film layers.

27. The method of claim 19, wherein the prostate surgery balloon device is constructed and arranged so that said fluid inflation causes sides of the prostate surgery balloon device to be drawn inwardly relative to said lumen axis.

28. The method of claim 19, further comprising disposing a valve in said inflation lumen.

29. The method of claim 19, wherein the at least two elongate film layers comprise at least two layers having different properties from one another, wherein said different properties comprise at least one of different thickness and different modulus of elasticity.

30. The method of claim 19, wherein the elongate compartment and subcompartments are constructed and arranged so that the prostate surgery balloon device articulates to said predetermined shape at pressure of said fluid in a range of from 1 to 10 pounds per square inch (psi).

* * * * *

UNITED STATES PATENT AND TRADEMARK OFFICE
CERTIFICATE OF CORRECTION

| | | |
|---|---|---|
| PATENT NO. | : 9,737,694 B1 | |
| APPLICATION NO. | : 15/336122 | |
| DATED | : August 22, 2017 | |
| INVENTOR(S) | : Tilak M. Shah et al. | |

It is certified that error appears in the above-identified patent and that said Letters Patent is hereby corrected as shown below:

In the Claims

Column 6, Line 6: "compartment that is ere configured" should be --compartment that is configured--.

Signed and Sealed this
Tenth Day of October, 2017

Joseph Matal
*Performing the Functions and Duties of the*
*Under Secretary of Commerce for Intellectual Property and*
*Director of the United States Patent and Trademark Office*